US008915863B2

(12) United States Patent
Shuck

(10) Patent No.: US 8,915,863 B2
(45) Date of Patent: Dec. 23, 2014

(54) IN VIVO DEVICE AND METHOD FOR RESEARCHING GI TRACT PROCESSES, MICROBES, AND VARIABLES ASSOCIATED WITH ILLNESSES AND DISEASES

(71) Applicant: L. Zane Shuck, Morgantown, WV (US)

(72) Inventor: L. Zane Shuck, Morgantown, WV (US)

( * ) Notice: Subject to any disclaimer, the term of this patent is extended or adjusted under 35 U.S.C. 154(b) by 0 days.

(21) Appl. No.: 13/930,558

(22) Filed: Jun. 28, 2013

(65) Prior Publication Data

US 2014/0163416 A1   Jun. 12, 2014

Related U.S. Application Data

(63) Continuation-in-part of application No. 13/691,169, filed on Nov. 30, 2012, now Pat. No. 8,491,495.

(60) Provisional application No. 61/727,177, filed on Nov. 16, 2012.

(51) Int. Cl.
*A61B 10/04* (2006.01)
*A61B 10/00* (2006.01)

(52) U.S. Cl.
CPC ......... *A61B 10/04* (2013.01); *A61B 2010/0061* (2013.01); *A61B 10/0038* (2013.01)
USPC ........................................................ 600/562

(58) Field of Classification Search
CPC ........... A61B 5/07; A61B 5/073; A61B 1/041
USPC ................................................. 600/562–572
See application file for complete search history.

(56) References Cited

U.S. PATENT DOCUMENTS

| | | | | |
|---|---|---|---|---|
| 2,881,756 A * | 4/1959 | Crosby et al. | | 600/565 |
| 3,057,344 A * | 10/1962 | Abella et al. | | 600/582 |
| 3,118,439 A * | 1/1964 | Perrenoud | | 600/582 |
| 3,485,235 A * | 12/1969 | Felson | | 600/582 |
| 3,528,429 A * | 9/1970 | Beal et al. | | 600/367 |
| 3,683,890 A * | 8/1972 | Beal | | 600/371 |
| 3,688,763 A * | 9/1972 | Cromarty et al. | | 600/572 |
| 4,036,214 A * | 7/1977 | Bucalo | | 600/582 |
| 5,170,801 A * | 12/1992 | Casper et al. | | 600/582 |
| 5,971,942 A * | 10/1999 | Gu et al. | | 600/582 |
| 7,449,001 B2 * | 11/2008 | Stoltz | | 600/582 |
| 7,452,338 B2 * | 11/2008 | Taniguchi | | 600/593 |
| 7,611,480 B2 * | 11/2009 | Levy | | 604/27 |
| 7,686,770 B2 * | 3/2010 | Cohen | | 600/568 |
| 7,717,862 B2 * | 5/2010 | Stoltz | | 600/582 |
| 7,740,595 B2 * | 6/2010 | Brown | | 600/565 |
| 7,938,775 B2 * | 5/2011 | Rabinovitz et al. | | 600/309 |
| 8,195,276 B2 * | 6/2012 | Uchiyama et al. | | 600/424 |
| 8,257,257 B2 * | 9/2012 | Takizawa et al. | | 600/302 |
| 8,343,069 B2 * | 1/2013 | Uchiyama et al. | | 600/562 |
| 8,394,034 B2 * | 3/2013 | Iddan et al. | | 600/582 |
| 8,406,490 B2 * | 3/2013 | Gat et al. | | 382/128 |
| 8,491,495 B1 | 7/2013 | Shuck | | |
| 2001/0051766 A1 * | 12/2001 | Gazdzinski | | 600/309 |
| 2002/0042562 A1 * | 4/2002 | Meron et al. | | 600/361 |
| 2002/0103417 A1 * | 8/2002 | Gazdzinski | | 600/109 |
| 2002/0132226 A1 * | 9/2002 | Nair et al. | | 435/4 |
| 2003/0020810 A1 * | 1/2003 | Takizawa et al. | | 348/68 |
| 2003/0085994 A1 * | 5/2003 | Fujita et al. | | 348/77 |
| 2003/0181788 A1 * | 9/2003 | Yokoi et al. | | 600/160 |
| 2003/0213495 A1 * | 11/2003 | Fujita et al. | | 128/899 |
| 2004/0092825 A1 * | 5/2004 | Madar et al. | | 600/473 |
| 2004/0115877 A1 * | 6/2004 | Iddan | | 438/200 |
| 2004/0122315 A1 * | 6/2004 | Krill | | 600/437 |
| 2004/0204630 A1 * | 10/2004 | Gilad | | 600/160 |
| 2005/0177069 A1 * | 8/2005 | Takizawa et al. | | 600/573 |
| 2007/0173738 A1 * | 7/2007 | Stoltz | | 600/562 |
| 2008/0208077 A1 * | 8/2008 | Iddan et al. | | 600/582 |
| 2008/0294143 A1 * | 11/2008 | Tanaka et al. | | 604/506 |
| 2009/0143697 A1 * | 6/2009 | Tanaka | | 600/565 |
| 2009/0253999 A1 * | 10/2009 | Aoki et al. | | 600/565 |
| 2010/0249503 A1 * | 9/2010 | Yazawa et al. | | 600/109 |
| 2012/0153981 A1 * | 6/2012 | Arneson et al. | | 324/756.01 |

FOREIGN PATENT DOCUMENTS

JP          05168639 A   *   7/1993   ............. A61B 10/00

* cited by examiner

*Primary Examiner* — Jeffrey G Hoekstra
*Assistant Examiner* — Michael C Stout

(57) ABSTRACT

An interactive research device comprised of an orally ingested capsule with pockets rendering the capsule capable of sampling intestinal tracts (gut) substances and microbes before, during and after delivery of system perturbation substances and methods of use and associate system are described. Sensors are provided to simultaneously measure, monitor, record, and transmit data in real time obtained from within the exact vicinity of substance deployment and location of microbial assisted digestive processes. In vivo collected samples are also collected and preserved for in vitro analysis. Digestive processes and dysfunctions involving proteins that result in "gluten sensitivities" and dozens of gut-based diseases that develop in stages, and have been mysteries for over 2,000 years, can be analyzed. The capabilities were developed to permit research within the heretofore inaccessible and important regions of the small intestine where villi functions are compromised, and in the upper colon. Special focus includes determining roles microbes and their byproduct substances in cascade play in autoimmune system responses and diseases.

20 Claims, No Drawings

IN VIVO DEVICE AND METHOD FOR RESEARCHING GI TRACT PROCESSES, MICROBES, AND VARIABLES ASSOCIATED WITH ILLNESSES AND DISEASES

This application is a continuation in part of U.S. application Ser. No. 13/691,169 filed on Nov. 30, 2012, now U.S. Pat. No. 8,491,495, which claims benefit of U.S. provisional application No. 61/727,177 filed on Nov. 16, 2012, the contents of which are incorporated by reference herein in their entirety.

FIELD OF THE INVENTION

The subject invention is a biomedical, bioengineering device and methodology for exploring, discovering, researching, analyzing, and characterizing specific biological microbial colonization and biochemical endogenous processes in the human gut. These processes are believed to hold the secrets to the causes of many diseases, of which are currently unknown, and for lack of technology, only their symptoms are treated or researched. This invention is intended to advance the fields of gut endocrinology, endoscopy, and microbiology by largely replacing the endoscopic and colonoscopy type tools currently available since much of the gut is inaccessible by these methods. This invention renders it feasible to not only obtain simultaneous biochemical and microbe samples in conjunction with a comprehensive sample gathering, handling, and analysis system, but to focus upon specific sections of the gut, the microbes, substances, and variables associated with those sections, in particular the small intestine and upper colon. This invention is designed to further isolate and characterize the specific strains of microbes, processes, and variables associated with specific illnesses and diseases associated with specific regions of the gut.

BACKGROUND OF INVENTION

In brief perspective, after 2,000 years and efforts from the best medical and research institutions using the most advanced technology available anywhere in the world, the actual processes and causes of Celiac, gluten sensitivities, and many other life threatening and taking diseases with origins in the gut, such as those resulting from gluten or other protein effects, remain unknown today. The fecal-oral cycle of pathogens entering the digestive tract has greatly increased in the U.S., due somewhat to more food sources from other countries, where sanitation is practiced less. Now, microbial diseases of the gut rank second in humans only to the respiratory system. While in vivo sampling of the respiratory and cardiovascular fluids is routinely performed with minimal cost, patient inconvenience, and time consumption, sampling of the gastrointestinal tract via endoscopic and colonoscopy procedures are more intrusive, costly, and more importantly of limited value or scope. It is estimated that of the more than 10,000 strains of bacteria, perhaps numbering well over a trillion in total number in the GI tract, less than 5% have even been identified/isolated, much less characterized within the gut or other environment. Much of the most important regions of the gut, first of all, are inaccessible for in vivo samples. As in virtually all in vivo sampling of the human body, analyses are performed in vitro. Once again, procedures for testing of gut matter, especially below the stomach, are in vitro collected samples and in vitro analyzed. Since not only is the second highest frequency of human diseases associated with the gut, arguably, the most serious and over a period of time, the highest number of serious diseases originate in the gut directly, or indirectly as a result of conditions within the gut. This should place extremely high national priority upon developing the capability of efficient, cost-effective, and technically-effective gut sampling and diagnostic capabilities. This invention is based upon addressing this national, and world-wide, need for improving human health. It is hoped that the research that led to this invention will also go far beyond the in vivo sampling of gut matter, and also lead to in vivo analysis and in vivo treatments of patients with a wide variety of illnesses and diseases in a relatively unobtrusive manner. The first invention by Shuck (U.S. patent Ser. No. 13/691,169), of which this is a continuation, is a serious accomplishment toward this overall objective, and the herein disclosed invention is step two, in the overall research and technology development scheme with the above stated goals.

These esoteric processes taking place in heretofore inaccessible regions of the gut contribute and lead to various stages of many diseases over several years in humans, and the initial, intermediate, and terminal stage symptoms all vary widely among human subjects. Implicit in this statement, and patient evidence, is that there are many, as in tens of thousands, of variables involved. Furthermore, these variables are not just of one scientific discipline, but several disciplines and the harmful effects are suspected of being caused by the interaction and creation of new variables resulting from the interaction or coupling of different scientific discipline based variables. An important implication is that due to the many variables, and the many disciplines combined, most of the research methodology used throughout history of correlating some phenomena using mostly statistical correlation methods, will never solve the mysteries of diseases associated with such protein digestion related processes, or other diseases with origins in the gut. The 2,000 year plus mystery is sufficient testimony.

Most research on Celiac and gluten sensitivities has been from individual disciplines of microbiology, gastroenterology, genetics, molecular biology, cellular biology, dietetics, bacteriology, biochemistry, immunology, allergy, toxicity, digestion, nutrient absorption, anatomy, physiology, etc. Naturally, since these problems are human health problems, they are researched primarily individually by the broad spectrum of disciplines associated with the human body and human health, and peripheral associated sciences and industries, such as pharmaceuticals. Unfortunately, there are many more disciplines that should be involved, but not significantly represented in Celiac and gluten-related disease research alone. Even the research methodology itself has been extremely limited because of the lack of appropriate technology. Also, the complex phenomena leading to so many different symptoms and diseases is believed to be of a more fundamental and complex "protein conversion process" nature, rather than just gluten, or some single antigen that provokes the autoimmune system. As reflected by the named disciplines above, most research also falls into investigation of the micro world level of processes. Even among the medical science disciplines, much research is mono-disciplinary, and very little research incorporates simultaneously variables from a variety of medical science disciplines. In reality, the esoteric nature of these diseases is hereby hypothesized to be a function of many variables from both the micro and macro world and spanning many disciplines. This narrow research methodology being practiced, however, is reflective of the world-wide culture of research. For a variety of reasons, researchers routinely do not reach out across disciplinary barriers. This is not productive in studying the gut!

On the contrary, the herein disclosed invention is associated with a broad research agenda based upon creating the capability for multidisciplinary research across many disciplines, even those far removed from the medical sciences, and involving both micro and macro world variables. In fact, the broad research scope is predicated upon proving that at least some of the significantly contributing variables are from non-medical sciences. In particular, such engineering sciences as fluid dynamics, mass and energy transport processes, diffusion and dispersion in porous permeable media, surface phenomena, boundary layer phenomena, physical chemistry, bio-reaction kinetics, surface chemistry, physical chemistry, etc. and all of the variables so defined within these disciplines are seldom if ever mentioned, much less, incorporated into the hypothesized, diagnostic or solution methodologies, or in any known models. In fact, models are not even considered as a rule, just some statistical correlation among symptoms variables.

Not only are these "other discipline" variables significant, but it is herein hypothesized that the products of the interactions of the "other" and "medical" discipline variables is where the causes and solutions will be found. These are the guiding principles which led to this broad spectrum research effort. The invented devices disclosed to date have the embodiments of Capsules A, B, and AB, and will be summarized with focus upon the herein disclosed invention of Capsule B. Further reference to research preceding this invention as in reference to Capsule A, and the broader research effort, may be found in the U.S. patent Ser. No. 13/691,169 by Shuck entitled, "Human Intestinal Tract Research and Diagnostic System To Evaluate Patients And Advance Medical Science And Bioengineering And To Determine Processes In The Gut And Causes Of Diseases". The ultimate goal, of which this invention is just one step, is of course to be able to cure many human diseases. Instrumental to this overall objective, is to generate the data and knowledge base for creating a biomedical-engineering model of the human gut encompassing all of the microbial-assisted, biochemical reactions and mass and energy transport processes. The innate nature of the gut is probably the world's greatest treasure of compact and diversified data spanning the nano to macro scale, and perhaps incorporating more disciplines of science and engineering than any other one object or functioning system on earth. By virtue of such already existing Big Data sets and the statistical combinatorial properties possible, such as factorials, permutations, and combinations, of the combined intrinsic gut system components and properties, along with appropriate definitions of hundreds of variables and their individual data sets throughout the GI tract, it constitutes a researchers dream world, yet stretches the limits of technologies when considering an appropriately designed research system and methodology for exploring, mining, and analyzing such data. That is the system, the challenge, and the perspective for this research effort.

SUMMARY OF THE INVENTION

This invention is based upon a continued rationale for first gaining access to all parts of the GI tract, sampling, testing and analyzing all aspects of the biological system, utilizing in the most productive manner the Big Data mined, discover disease causing processes and interrupt them, and ultimately characterize and create holistic models of the gut system. Access and information mining is accomplished in 3 steps of which this invented device, Invention 2 Capsule B, is the second step, and like step 1, Capsule A, it uses a belt system to simultaneously collect samples of microbes and substances within the human or other animal gut, and preserve them for later in vitro analysis, but in addition, to also deliver substances or objects to the gut in specially designed pockets of belts for either use as part of the process or functions to be performed as the Capsule passes through the gut, or to be accessible to microbes for processing. In particular, the Capsule can be allowed or commanded to, while in a particular region of the gut corresponding to specific anatomy, release substances protected from upper gut enzyme and acidic environments, thus of controlled composition, to be consumed or interacted with microbes within said region, and immediately and simultaneously sample the associated microbes and chemical substances and preserve them for later in vitro analysis. Release or exposure of the substances to microbes can be controlled over predesigned desirable times and distances repetitively within the gut, and samples, of 50 to 100 or more, can be collected in immediate capsule vicinity, upstream and downstream, to provide fine resolution of the results of such substance interaction with microbes, in particular of such microbe strains as may have a special affinity for particular substances, or as may create certain measurable conditions or processes of interest. The invention provides for the reduction of perhaps thousands of variables to hopefully a few hundred or much less, for the purpose of discovering the specific microbes and their biochemical created substances, such as toxins, associated with specific diseases, and the specific processes through which the autoimmune system and other anatomical components of the gut, such as the villi in the small intestine, are interrupted and corrupted from performing their intended functions, which directly leads to increasing stages of various illnesses and diseases. The ultimate result is intended to create explanations, understandings and conclusions pertaining to gut functions and gut based illnesses and diseases, based upon basic science and engineering principles and processes, instead of statistical correlation of extra body symptoms variables.

DETAILED DESCRIPTION OF INVENTION

The Enabled Research Methodology of Invention 2, Embodiments of Capsule B

Issues Defining the Parameters, Features, and Requirements for the Invention

The necessity of isolating from thousands, the pertinent combined and interdependent micro and macro variables, in a longitudinal, multi-dimensional, multi-disciplinary process within the gut, demanded the creation of a system, such as the belt, comprising dozens to hundreds of isolated and protected pockets for a variety of uses in a controlled and sequenced manner Samples of time, spatial, microbe-specific, and in cascade manner, dependent data are required to provide the capability of isolating the numerous multidisciplinary variables. More, specifically stated, the generalized protein-based illnesses in humans, such as Celiac and autoimmune responses, is hereby hypothesized to be caused not directly by the proteins, including gluten, but by the microbe species or combinations of species or strains, and their biochemical byproducts, and even resulting from multiple microbe species/strains processing of byproducts in a cascaded manner Thus, these microbe-actuated, biochemical processes create toxins, that in turn cause autoimmune responses, along with other coupled macro and micro phenomena over a period of time, that lead to the wide variety of 100 or more symptoms in varying combinations, and ultimately diseases in different human organs that develop in stages over extended periods of time. No simple research methodology involving 2 or 3 variables from within just one or two disciplines, especially using just simple statistical correlation methods, and using symptoms-based variables, will ever solve the problems and mysteries of Celiac or gluten sensitivities, or many other illnesses and diseases with origins in the gut! An accidental discovery of a simple process with a simple cure, as with *Helicobacter pylori* infections being the principal cause of stomach ulcers, is beyond unlikely. Once again, this is the direct rationale that led to the necessity of the broad scope research effort, and in particular, the herein disclosed invention as a critical step.

The noninvasive and convenient use of an orally ingested capsule in order to avoid all of the typical medical facility protocols, costs, and time consuming procedures is what makes most of the herein disclosed invention practical and highly desirable, if not necessary. The detailed, fundamental functions of Capsule A as a passive sampling and data gathering device have already been disclosed, discussed, and referenced. In brief summary, Capsule A, met the need to explore and sample simultaneously with great resolution, the microbe world and associated chemical substances throughout the intestinal tract. It also further accommodated the preservation of each sample collected along the intestinal tract, which could include up to several hundred samples. Capsule A further allowed sampling of the "as-is" conditions within and along the entire gut in a relatively non-intrusive, non-disturbing manner both to the patient and the gut environment being studied. This capsule could sample for any specific diet, or orally, or intravenously administered drugs to determine the distributed in vivo effects, as would later be measured by in vitro sample testing and analysis. Prior to this invention, no other methodology provided even this capability. Unfortunately, even with this invention and its very important contribution to analyzing the gut, any food ingested as part of dietary studies is still subject to the entire environment of the digestive tract starting at the mouth and proceeding through the acidic and enzyme attacking chemicals of the stomach, and the multitude of processes along the colon.

This leaves the problem of bypassing or isolating and avoiding the effects of all of the upstream variables and conditions interjected and imposed by the digestive processes from the mouth to at least the duodenum or pyloric sphincter muscle before the main processes of interest take place. A device or method was needed that eliminated this long list of interjected and problematic variables, and that bypasses the entire mouth to duodenum hostile environment. The more serious human illnesses and disease processes of interest are those taking place in the conventionally inaccessible small intestine that destroy the villi or corrupt the villi processes and functions which they normally serve. This region is inaccessible by known technologies such as endoscopies and colonoscopies, which leaves several feet of the gut in vivo processes unexplored. The lower ileum-upper colon is also a region of major interest. The in vivo measurement of variables from zonal-specific, isolated and preserved samples within these zones of the gut has heretofore not been possible. In addition, conducting experiments exclusively within this zone and collecting protected in vivo samples with the immediate adjacent and simultaneous effects as a means of variable control and isolation, and elimination of extraneous variables has not been heretofore possible. Thus, some of the parameters guiding the invention of Capsule B have been identified. Capsule B serves three major purposes: 1) elimination of extraneous variables, 2) providing for the introduction of new control variables within this extremely important region of the small intestine and upper large intestine, and 3) measuring the results or consequences of exercising said control variable experiments. This Invention 2 Capsule B now constitutes another valuable research tool with only these three new capabilities. It is quite significant that Capsule B allows all of these multidisciplinary variables and influences from the mouth to the duodenum to be eliminated if desired as an option, and control variables can then be introduced in vivo at the point of interest within the gut, and the immediate and simultaneous effects can be sampled for later in vitro measurement and analysis as a function of length or exact position within the gut, which is of paramount importance, and heretofore not possible.

The next step in the research phase rendered feasible by Capsule B, is to isolate variables of interest, and then introduce control variables, and in particular, the most significant, multidisciplinary ones. Capsule B has now been distinguished from Capsule A, as well as, current medical methodology. In stark contrast to current methodology, whereby medications are administered in a variety of ways, and then extra-body, in-vitro processes of all types, ranging from cultures of specimens to body function measurements are used to diagnose effects using largely statistical correlation methods. This current methodology will never solve the herein discussed problems. The hypothesized nature of gluten, or protein in general, based illnesses and diseases will require an "in vivo" based methodology, upon which this invention is based. Since the phenomena are time and spatial functions of multidimensional, multidisciplinary, coupled variables, the diagnostic methodology and specifically required tool or tools, must have these associated capabilities. This rationale further formed the basis of this Invention 2 with embodiments of Capsule B. In contrast to Invention 1 with embodiments of Capsule A, which is a purely passive, unobtrusive tool, Capsule B has in addition to the capabilities of Capsule A, the "active" ability to introduce in vivo controls, import substances, and control variables, and measure the results, all of which still pertain to the same species and class of biological science as Capsule A.

As one means of reducing extraneous variables and discovering the strong variables believed to be associated with many gut diseases, Capsule B allows specific foods ingested by humans, and already known to be the superficial indicator source of gut problems, to be introduced at any specific point where anticipated problematic processes are first initiated. Although Capsule B allows test food to be introduced or interjected at any point in the gut, the particular chosen point depends upon the research test objectives and plans, including, for example, how much of the digestion process would be selected to be included in the study.

Example

Consider momentarily only one very important example. Capsule B allows interjection of food to be initiated in:

a). the bottom of the stomach in the chyme where the pH is still around 2 and microbial flora are minimal, yet many of the macromolecules have been digested, or b). in the duodenum or jejunum where the pH is increasing to 4 or higher, yet digestion is continuing, and microbial populations are increasing, including those unknown suspecting problematic species/strains, that may have taken up residence there.

This flexibility in strategy in itself could potentially reduce the number of extraneous variables, since largely Enterococci and Lactobacilli bacteria are the major populated known flora down to the ileum in healthy individuals. Of interesting coincidence also, are two other very important considerations for this region of the gut. The in vivo, real-time environment of the jejunum is perhaps the most inaccessible to research and where many microbial-assisted biochemical process mysteries reside. In addition, this section of the gut is the major home of the villi and micro-villi gut lining, so critical to energy and mass transport processes through which the human body converts and extracts its energy, and obtains the nutrients that feed many organs of the body, from head to toe! It is noteworthy that microbes also have special nutrient requirements and food preferences, sometimes in competition with themselves and the human body, and sometimes in symbiotic relationships. Deficient nutrients to any organ over time can lead to a variety of diseases in that organ! The capabilities of Capsule B to take many samples simultaneously both upstream and downstream of introduced substances can be extremely valuable in analyzing and discovering the processes involved when gluten, for example, is processed in a given microbial environment, and forms a thick, viscous encapsulating layer of a viscoplastic substance over the villi, that for both obvious and unknown reasons, lead to their dysfunction and demise, including their shrinking, and dismembered disappearance from the gut walls, as observed from autopsy! The causing complex processes remain unknown.

However, many symptoms of gluten related diseases also indicate complications in the large intestine where the pH reaches 7, and all oxygen is consumed leaving a pure anoxic environment where only anaerobes exist. The problem is that enormous populations of many strains and species of bacteria reside there and greatly increase the number of variables for necessary consideration. The fact that important bile acids and vitamins, including vitamin $B_{12}$, are absorbed in the colon makes it a prime subject for investigation. Vitamin $B_{12}$ deficiency is a prime symptom of gluten affected patients, as well as, the elderly visibly-healthy individuals, who experience weakness and low energy levels. What process is interrupting the propionibacterium creation process, or the absorption process? Orally taken $B_{12}$ is not effective, so $B_{12}$ shots intravenously administered are necessary. So what are the gut processes that are compromised, interrupted, or corrupted! While these examples are real and serious, they represent only a small fraction of the functioning and application of Capsule B, and the urgent demand for such an in vivo research tool? Without the capabilities to conveniently, and almost whimsically, research all of these areas in vivo, involving the hundreds of otherwise un-measureable variables, would essentially render no hope for ever solving the causes of these gut mystery diseases. This single example alone, illustrates the extremely important roles this Invention 2 and the embodiments known as Capsule B can play in medical research, including the introduction of entirely new research methodology. In this regard, the gut is usually thought of as just a one-way delivery process. However, use of Capsule B can explore other organ feedback, perhaps even interactive, means with the gut, including that gut feedback communication process from the human brain by some electro-biochemical means, or muscular or other physical means.

General Apparatus or Device Capabilities

The apparatus or device features that create this capability over Capsule A, include a variety of changes to the belt and its pockets or indents as used originally to just capture samples in the pockets and preserve the contents of the pockets for in vitro analysis. As previously described for Capsule A, a micro-motor driven belt capable of capturing gut matter samples in small pockets and sealing those pockets with a hermetically sealing film to protect and preserve the integrity of said samples was used in the sample collection process. What is now disclosed is likewise one or more belts, but of different design, purpose, mode of operation and function, and involving different products and their utilization. In this case, the differently designed belt(s) serve four distinctly different purposes, which can be used individually or collectively in combinations, including all four simultaneously.

These four purposes include:

In addition to Capsule A sampling capabilities, two additional belts in Capsule B are designed differently to also transport matter or objects into the gut, to serve a plurality of purposes, including:

1) substances of a variety to serve different purposes, such as microbe baits, 2) multi-purpose measuring instrumentation, 3) multi-purpose control means and systems of actuators and telemetry antenna to serve a plurality of applications, including both internal Capsule and external telemetry monitoring and control, and 4) Incidental to any and all specific combinations of these first three purposes and capabilities, collect in vivo data of circumstantial evidence of direct response behavior that will lead to proof of hypotheses and causes of gut biochemical and microbial processes, that among other things, result in autoimmune system responses, illnesses and diseases, and then ultimately lead to cures for gut diseases.

The measuring instrumentation may, for example, include measurements of macro body properties such as pH, temperature, noise, or other biochemical gut process variables, that can be measured, especially as consequences of introduced special foods or other substances. This may even include very importantly, the ability to recognize and distinguish between different molecules by any means of any individual molecular properties. Of particular example is recognition of toxins produced as part of bacterial assisted digestive processes. Recognition of said toxins may be by macro fluid variables, such as pH, noise, temperature, or by such micro properties as molecular shapes, movements, vibrations, communications, or other distinguishable features, etc. Such capabilities being considered are currently emerging micro technologies, involving bionanotechnology sciences with such applications as graphine, one atom thick layers of carbon on substrates, that form the basis of micro-type sensors incorporated into microchips. The control means may include both feedback, and feed-forward processes in an engineering sense, and said processes may be both animate and inanimate, individually and in combination, in nature. The animate nature may include all microbes, from viruses down to single cell animals, up to larger microbes of bacteria or larger, even macro size. Initially, special emphasis is placed upon using the inexpensive, readily available lab-on-a-chip technology, including cell-on-a-chip and organ-on-a-chip methodologies. Cells-on-a-chip are of special relevance and importance because of probable reversibility application in the detection, isolation, and characterization of toxins to the autoimmune system. The inanimate nature includes chemicals, and biochemicals as may be produced within the gut by microbes, as well as, for example, microchip based control means, and hybrid animate-inanimate means.

Capsule B Apparatus

The manifestations and research capabilities of Capsule B, are accommodated and implemented by special features, primarily the two major components, a housing, and a cartridge that contains belts, motor, battery and peripherals. This simplicity of design is one of the attractive features of this invention. The Capsules are intended to be used by clinicians and researchers in an efficient manner not requiring extensive training. This design concept is intended to not interject obstacles or distractions for application. The apparatus features are associated with current perceived test applications. Modifications of the housings or the belts do not require any significant engineering beyond that of a technician to accommodate new variations in emerging applications.

Housing

The housing largely resembles that of Capsule A previously described, and consists of a circular cylinder type shell or enclosure, and two domed end pieces with male threads that screw into the cylindrical shaped main housing body with fine female threads, and grooves for accepting O-rings as seals effectuated by the threaded mating parts, and a guide track fastened to the inside walls to receive, position, constrain, and allow easy installation and alignment of belts without any special knowledge, skill, or tools. Different main housing bodies are designed with special purpose ports to accommodate and match up with specific design belt configurations as mating parts with suitable tolerances and allowances. Variations in the housing ports include: sizes, shapes, orientations, and positions within the housing body. These differences result from the mating part requirements of different belt configurations to accommodate specific tests. The port geometries are associated with the functions to be performed by each belt corresponding to specific experimental tests. In general, there are three basic port-belt associations involving: 1) sample extractions from the gut, 2) substance delivery to the gut, and 3) associated sensors, transducers, actuators, and transmitters.

Belts

The belt, as a basic design concept, provides the greatest versatility in conjunction with simplicity as a means of accomplishing many tasks associated with the broad test objectives, purposes, functions, and tasks necessary in such a biomedical environment, and such a complicated anatomical system as the subject being investigated and treated. The belts incorporate three basic covers as a means of protecting substances delivered to the gut and the integrity of samples recovered from the gut, and protection needed in some cases for the tools, either from the gut environment, or the gut from some of the tools themselves. Since the complexity of the gut anatomy and processes taking place therein introduces multiples of hundreds of combinations of variables, the belt was conceived as the only practical means of meeting the demand. As such, belts can be configured for prescribed tests. The different purpose belts are configured on cards as cartridges ready to fulfill different test applications, and to be slid into the housings. Likewise, there is a diversity of belt pocket sizes, shapes, numbers, and orientations, in configurations and combinations in any given belt, to accommodate a battery, micro-motor, and provisions for each test. This concept addresses application to current issues and provides for immediate adaptation of new belts to meet new medical research needs. That is, this design utilizing the belt means, can efficiently respond immediately with minimum time, adaptation, and cost, to evolutionary research and treatments based upon future medical profession needs yet to be discovered, especially those as a direct result from usage of Capsule B capabilities and the new research methodologies being introduced that broadens the horizon of gut medical science beyond the gut, to the entire human and its many anatomical components.

Various Other Design Features

An obvious goal, of any ingested object for any purpose to engage in in vivo exploration or treatment, must include many considerations as pertain to health concerns, anxiety associated with ingestion of the capsule, and comfort in general for the subject ingesting the object. Such concerns must include the possibility of internal damage to the human subject as a result of usage of the device, including the possibility, however remote, that said device could get stuck or lodged somewhere within the intestinal tract. Therefore, anticipation of such problems must be incorporated within the device design features, along with contingencies for any accidental situation that might occur. It is with this mindset that other design features were incorporated into the invented Capsules.

There are some innovative opportunities available involving the selection of materials used in construction of said Capsules, and most of their components. Obviously, no material considered to be a potential toxin or health risk can be used for any part that could not effectively be recovered within a matter of days, if not hours. There is an opportunity, in some cases, to utilize actual food substances safe and suitable for human consumption, and even perhaps, decomposable as part of a digestion process, in some of the components. Capsule components considered suitable for such consideration include: housing, cards, card guides, belts, pockets, pocket covers, O-Rings, and some tools. One example material is celery strings, which possesses tensile strength and other properties suitable for various purposes. More immediate implementation of materials is achieved by using several 3-D printing materials already approved by the FDA as being safe for use in biomedical applications. Even further consideration is given those FDA approved materials that have susceptibility to dissolving when subjected to digestive tract juices at particular gut locations.

Also considered in contingency plans are rescue means and devices. One particular Capsule design embodies the capability of delivering one or more substances in belt pockets as a "rescue measure, or entire vehicle", wherein either dislodging or disintegration into small fragments could insure clearing the intestinal tract completely of any Capsule components, and without any surgical procedures, and perhaps, even patient administered in some cases, but for the highest scientific method based probability for success, assisted by the telemetry remote control system normally used. Such rescue procedures could include, in addition to oral laxatives, such foods as vinegar or olive oil housed in a belt pocket, or even a separate rescue Capsule that could release the vinegar or other substances, adjacent to any lodged capsule, wherein the shell and some other components could be disintegrated safely within the gut. Some other components, such as a micro motor or battery incorporated into another isolated pocket of the belt would be of sufficiently small size (<10 mm) that it could be readily passed through the intestinal tract unobstructed. Any potential lodging would likely be in the region of duodenal cap, or pyloric canal. The pyloric sphincter muscle has a normal resting diameter of 7 to 10 mm or greater, and passes objects up to 10 mm diameter or larger even without contraction when confronted with peristaltic or other pressure waves. Thus, safety and discomfort of the patient has been given due consideration in design aspects of herein disclosed inventions.

Relevance to the U.S. National Institutes of Health (NIH) Project Known as the "Human Microbiome Project (HMP)".

In brief summary, this 5-year project was launched in 2,007, largely as a feasibility study, to identify and characterize the microbial flora associated with the human body of healthy and diseased individuals, and with a total budget of $115 million. The thrust of the project includes culture-independent methods of microbe characterization, such as, metagenomics, and whole genome sequencing, of which 3,000 such sequences of individual isolates were planned. Also included were deep sequencing of bacterial 16S rRNA sequences amplified by polymerase chain reactions. Five body sites of oral, skin, vaginal, gut and nasal/lung were included. Some 200 scientists at 80 institutions participated in the U.S. project and sequenced genetic bacteria from 250 healthy individuals. Similar projects are underway internationally, and being coordinated by the International Human Microbiome Consortium. The Canadian similar effort to look at microbe colony alteration associated with chronic disease is being coordinated through the CIHR Institute of Infection and Immunity. In other words, the world medical scientific community is finally focusing on this extremely important aspect of human life.

It is truly unfortunate this invention was not available to be a part of the original logistics for planning, much less, identifying and characterizing the flora of the gut. It is also unfortunate that this researcher was unaware of this HMP project until just a couple of months ago, and a couple of years after when he first pursued these inventions independently, whereas, being a part of such a program may have expedited the arrival and development of this invention and it could have even been used within the initial program. In summary, Capsule A and Capsule B herein disclosed are close to being dream tools for such a project. In fact, their capabilities far exceed the needs and requirements for human gut sampling needed for this HMP project, not only for the most important gut areas, but the entire human gut at one pass under identical conditions such that an entire gut microbe roadmap and profile could be created for specific individuals. Sampling the gut at only a few isolated points is not necessarily meaningful, because the upstream and downstream microbial colonies are believed to have co-dependencies and interrelationships at each and every point, which is believed to be instrumental in disease processes. So it is the closely spaced distribution of diverse colonies and species, as well as their individual byproducts, that becomes really important, especially in unhealthy individuals, and precisely for such research the herein disclosed Invention 2 is intended to serve!

APPLICATION EXAMPLES

The utility of Capsule B, especially when combined with Capsule A, opens up another world of opportunities and perceptions of the gut to tantalize the imagination of researchers from many disciplines within many branches of science and engineering. Some specific applications which led in part to these inventions are listed below, just for illustration.

Now, with Capsules A and B, access is feasible for the first time, to the entire length of the gut in a continuous manner, with small incremental sampling, with any chosen resolution over any section of the gut or its entirety as a function of length "x". This capability enables an entirely new perspective of how to experiment, analyze, and model the gut. Consider, for example, the need and ability to construct discrete, numerical polynomial functions of unlimited numbers of variables $V_i$, as a function of x. Let's call these "distribution functions", where the distribution functions may include:

Experimental-Data Based Distribution Functions a) $M_{i,j}=f(x)=$Microbe species "i", strain "j" population distribution functions b) $CHS_{m,n}=f(x,$ specific diet$)=$chemical substances distribution functions based upon specific diets c) $pH=f(x)$ distribution function d) $F_k=f(x)$ microbe preferred foods when given multiple, simultaneous options distribution function e) $T_1=f(x)$ toxins to autoimmune system distribution function for healthy and ill humans f) $O_2$ anoxic environment$=f(x,$ proteins, microbes, - - - etc.)

g) or $CH_4$ or sulfur gas based compounds$=f(x,$ diets, proteins, microbes, - - - etc.)

and these experimental-data based functions can be analyzed in a wide variety of ways, including:

from simple multi-dimensional graphical overlays or superposition, to statistical auto and cross correlation methods, sensitivity analyses, or other profile data analysis methods, etc.

At this point it becomes obvious that this device and methodology, when coupled with other complementary apparatuses, testing and laboratory equipment, will generate huge, unprecedented data quantities and information on the gut, its processes, and manifestations within the body as pertain to mass and energy transport, nutrients creation, and distribution to other body organs.

Calculated Data Functions

In addition to raw data obtained from various designed experiments, data analysis and interpretation using such methods as cross plots or combined functions, etc will also generate huge volumes of data. In addition, for each raw or processed data set or variable function, there may be several calculated or model generated variables or variable functions, such as, 1) $T_1=f(F_k, x)$ Toxins$=$function foods or microbe preferred foods distribution functions 2) $T_i=f(M_{i,j}, x)$ Toxins$=$function of microbe species and strains distribution functions 3) Statistical history matching of variables a), b), c) - - - e) e.g. in patients with various illnesses and diseases Thus, this invention takes us from a "little or no data" situation to mountains of data, as in "Big Data", in only a relatively short period of time and applications! From a technology perspective, this is both fantastic, and a challenge to employ data animation in conjunction with multi-dimensional graphical means to facilitate getting this information to both, other researchers and practicing physicians, in a convenient useable format for their own interpretation, yet one that efficiently conveys the content and esoteric messages therein contained. This invention does have hierarchical or structural features in 1) design and 2) in data reduction, analysis and usage. On the one hand, it is first and foremost intended to be as simple as possible, in principle of construction and operation, to get the highest priority result of discovering causes of gut diseases. The second level features are to emulate to the point necessary the characteristics of the system being investigated as a means of compatibility in sampling, testing and characterizing it. In this respect, variations of the Capsule B are needed utilizing the most capable, miniaturized and advanced technologies available to adequately correspond with the sophisticated environment and mine the Big Data sets inherently available and waiting to be explored and analyzed. Of particular relevance and importance to the overall mission is the manner in which all of the accumulated data and information can be made available to the entire medical and scientific research community, and how it can best be used to characterize and model the human gut as a means of creating a more holistic understanding of it and its complex functions. In this regard in particular, Big Data methodologies will be explored to synthesize models of behavior and function, and ultimately use in diagnostic, and perhaps, treatment procedures. Hopefully, the simple interactive, real-time sensing and DF diagnostic and treatment schemes introduced in this combined system to yet be described can be highly developed to provide perfected gut diagnosis and treatment.

In summary, this stand-alone Capsule B device and method invention is intended to reflect a new methodology for the determination of the causes of gut-source illnesses and diseases as part of a system for a new approach to gut-related human health, as compared to the limited current methodology of extra body measurements and statistical correlation of symptoms from in vitro measurements! The role of this invention is to research and ascertain functions and responses of the gut as a system. In the process of further explaining the digestion process, as well as, the sources of gut based illnesses and diseases, a new perception of the gut and its functionality should result.

PRIOR ART

Search of prior art did not reveal any related to the above belt-based system and capabilities, especially, as pertains to the belt with pockets unique existence, utilization, and all component and functions pertaining thereto, of which, are all embodiments of the below claims. That is, all of the herein claims and functions are due to the flexibility and unique opportunities provided by utilization of belts and their diverse pocket designs. The stated intent and purposes of uses also draw distinctions in inventions. Therefore, these claims offered as Invention 2, Capsule B are believed viable, at least with slight modifications, or as may be amended upon examination.

The closest prior art to these claims is believed to be largely and foremost that of two patents, the first being U.S. Pat. No. 7,686,770 B2, dated Mar. 30, 2010, by Cohen, wherein a capsule with an excavating type, sprocket-driven, chain-like mechanism, with buckets or claws thereon resembling a chain saw, rake in samples from the gut in what appears as a hazardous operation. This sample method collects and comingles all samples into some common receiver, thereby not conforming to any of the purposes, designs or methods herein invented. Therefore, there is little resemblance of this invention in design, functions, applications, or otherwise to the invention herein disclosed.

The second and perceived closest prior art to the subject invention is believed to be US 2005/0177069 A1, dated Aug. 11, 2005, by Hironobu Takizawa, et. al., entitled "A Capsule Medical Device". Since this invention is the one of closest similarity, its features will be examined in detail for comparison purposes, and thus, they are first summarized below.

The Takizawa device has similar appearance of a cylindrical cylinder with hemispherical ends, wherein no method of assembly/disassembly or structural means of placing internal components is described. The salient features of this device as disclosed comprise:

1. a chemical sensor with a recovery device that includes a cleaning solution holding container, and cleanses and resets the chemical sensor to an initial state suitable for a plurality of reusing cycles, or continuously. Capsule B does not claim this capability.

2. provisions for opening/closing a port in housing by sliding a cover back or forth to expose sensor 3. a sensing circuit that senses output from sensor and sends data, as suggested by diagram wirelessly, to a receiver located outside the body for a predetermined time interval, upon which time interval being completed, the recovery operation begins by closing cover and initiating the reset process, which includes solution cleaning of sensor, drying sensor surface by included heater, and being positioned to repeat the process by once again opening the cover to the sensor.

Somewhat similar, but different in execution, purpose, method, and functions, 4. an internal battery Capsule B does not include this as a specific, single claim.

5. a heater and piezoelectric crystal driven vibrator driving circuit for cleansing and resetting chemical sensor Capsule B does not claim this specific capability.

6. a capsule medical device with 4 modifications allowing 11 embodiments of functions of said capsule. In one modification gut fluids are sucked in, filtered, and used to clean surfaces of chemical sensors. Capsule B does not claim this capability 7. a control circuit, extracorporeal sensor output level detector and level marking instructing signal receiving marking mechanism employing a discharged permanent gut wall marking agent which is deposited externally through a hole in housing to gut wall so said point can be located in future capsule deployments. Capsule B does not claim this capability 8. 4 external housing mounted chemical sensors always exposed to gut fluids to detect tumor or bleeding and a plurality of housing openings where sensors are located inside said housing at each opening. Somewhat similar, but different in execution, purpose, method, and functions, 9. The chemical sensor detects the target blood or fluid contents and its electrical or optical properties are changed by the fluid contents deposited on the surface of the sensor. In another embodiment an optical sensor is used to examine fluids deposited on chemical sensor. Another embodiment includes fluids filter, clear glass tube, various light sources, and light wave lengths, and reagents usage means, for purpose of examining gut fluid contents detecting blood and measuring pH, Somewhat similar, but different in execution, purpose, method, and functions, 10. Thousands of micro electrodes constituting an array on a substrate detect Somewhat similar, but different in execution, purpose, method, and functions, and Capsule B does not claim this specific capability 11. LED and CMOS imaging means deployed from one hemispherical end of capsule suitable for detection of previous capsule excursions and gut wall markers.

Capsule B does not claim this capability.

12. Films are exposed to gut fluids and analyzed using reagents, light emitting, and light transmission, piezoelectric controlled focusing means, and transparency methods to characterize the fluids. Capsule B does not claim this capability.

13. Means are provided for depositing digested substances from stomach, small and large intestines on films, but for what purpose or analysis not included in discussion or the 65 claims, although presumably in conjunction with overall purposes and methods as stated above in descriptions 1 through 12. Somewhat similar, but different in execution, purpose, method, and functions, and Capsule B does not use the method of depositing substances on films.

Relevant Prior Art Comparisons and Differences from Herein Listed Invention 2 and Claims Since the Takizawa invention represents the closest art, specific comparisons and distinctions are made with it.

1. The purpose and embodiments of the Takizawa, et. al device, however similar in a few respects, are focused on locating tumors or bleeding locations along the intestinal tract (gut) wall, marking the location, returning to the location in another capsule excursion, and examining and treating said tumor or bleeding abnormality.

2. The purpose and embodiments of herein disclosed inventions are grossly different. In contrast, not only is the present Invention 2 different in purpose and operations performed, but the means of implementation of all operations of said Capsule B, however similar in operation or method to Takizawa, are different in other respects, in that the embodiments are provided as a result of the means created by belts with compartments containing the sampling means, substances, and tools and as a result are of different and improved methods of articulation, deployment, and exercise of all operations are executed by different means of even the closest similar operations of the Takizawa device. Therefore, Somewhat similar, but different in design, execution, purpose, method, and functions, 3. It might be observed that the Takizawa device would serve a great complementary purpose and capability when used in conjunction with the purpose and capabilities of Inventions 1 and 2 to provide an even more capable and comprehensive system, since they are distinctly different in capabilities and provide mutually exclusive, different results. Combined, these different devices would give practicing physicians, clinicians, and researchers more comprehensive options and an additional tool to help solve the mysteries and causes of gut illnesses and diseases, and perhaps, an enhanced ability to treat them. The herein disclosed Invention 2 does provide overlapping capabilities wherein said Invention 2 with minor belt modifications can perform virtually all of the operations as evidenced and disclosed by Takizawa, but the reverse is generally not true.

Specific Distinctions Between Invention 2, Capsules B, and Takizawa Device.

1. Capsule B embodies belts comprising pockets of various sizes and configurations that accommodate the storage, protection, deployment, and retrieval of substances and various instruments or tools analogous to a tool box. Said belt pocket contained instruments/tools are capable of delivering masses to, or retrieving masses from any portion of the gut at any point or time during its passage through the entire GI tract (gut), and in substantial quantities and closely spaced intervals upon command. The Takizawa device does not have this general capability or similar means of accomplishing lesser tasks.

2. Capsules A and B, are designed with purpose of simultaneously sampling at small incremental distances along the gut, upon demand/command, at the exact same time, both digested substances and the associated microbes contributing to those digestion processes, with explicit purpose and protocols of searching for chemical toxins, microbe feces, as produced in serial cascaded fashion, with intent to diagnose, analyze, and construct models of said gut processes. This requires collecting, preserving/protecting and delivering sufficient sample sizes in pockets suitable from a single sample for a multitude of analytical chemistry and instrumentation analysis methods, including, mass spectrometers, spectrophotometers, culturing, traversing-scanning electron microscopes (SEMs), etc. This distinction is unique and requires unique capabilities not found in any prior art, including that in any of Takizawa's 65 claims.

3. Administration of a substance to the gut as provided by the Takizawa device is accomplished by first detecting and selecting and marking the location in one gut capsule excursion, and then returning to that marked location with another excursion, wherein in contrast, A and B provide for near simultaneous sensing and subsequent delivery upon command treating substances as provided for by different belt pockets in a single excursion of the gut.

Certain pockets within said belt(s) are indexed for selection and deployment into service, independently or simultaneously, either to deliver, or sample, mass upon command at any point in time "t" or location "x" along the entire GI tract. Said indexing is accomplished by telemeter remote switching, using reversible and/or stepping micro-motor driven belts. There is a Belt 1 that is a sampling belt with start/stop provisions and sealed identical as in Capsule A, but in addition, is divided into two belts 1-*a* and 1-*b*, that straddle an in-between belt 2, which is used for mass delivery and the pockets are opened or closed upon command. One Purpose of this arrangement is to create the capability to inject matter, of any substance or microbe, into the gut at any time "t" or point "x", and immediately in the same vicinity, and simultaneously measure the consequences of said injected substance on both sides of the injection to prove cause/effect relationships. Said straddle arrangement provides the capability of measuring said consequences, or system perturbation, for any upstream or downstream orientation of Capsule B within the gut, since its elongated shape will result in one or the other positions within the gut. Furthermore, wherein said straddle belt arrangement eliminates uncertainty in cause/effect relationships, and greatly reduces by orders of magnitude in this case the number of extraneous variables for analysis and modeling purposes. Such elimination of orders of magnitude of variables can greatly enhance microbiome associations, different taxonomic level and taxometric investigations above species to below strains or alleles, and for example, sequencing at the taxonomic phylum level of microbes associated with individual foods, or proteins.

A third belt 3 may be positioned adjacent to one other side of belts 1-*a* or 1-*b* and containing a plurality of sensor/transducer/transmitter components inside individual belt pockets that can individually or in combination, be selected upon command to expose sensors/transducers to the immediate gut environment (without interference and prior to, during, and post injection of substances from belt 2) to immediately measure cause/effect relationships with background data simultaneously of any detectable changes, of any detectable phenomena, and of any disciplinary nature. Exposing sealed sensors upon command prevents sensor exposure to the hazardous acidic conditions of range pH of 2 or 3 in the stomach, unless otherwise chosen. Examples of said sensors include, but are not limited to, noise or acoustic waves, pH, temperature, pressure, electrical conductivity/resistance, opacity, reflectivity.

Following a period of exposure "t" of substances in one or more belt pockets to the gut environment, the pocket is closed and sealed suitable for solids, liquids, gases, and microbe, later in vitro sample analysis. One example of purpose is the substances contained in the pockets may be specific microbe baits, or other FDA approved chemicals, or other foods that when processed by microbes create or possess specific chemical, electrical, physical, toxicity, or other distinct characteristics, that may lead to an understanding of gluten based toxins that create an auto immune response, and said toxins can thereby be analyzed as to origin, process and content. In as much as passage of food products through the gut, and their digestive process is a function of time, it is further claimed that this invented method and process allows not only for a single snapshot sample testing, but a dynamic, time-dependent digestive process to be sampled (and thereby in vitro analyzed) in a semi-continuous or discrete sampling manner, and simultaneously, due to multiple belt pockets, including determining direct cause/effect relationships anywhere within selected sites, and throughout the entire GI tract in one pass.

Belt 2 pockets may contain substances that can be released, in any however improbable situation of the capsule B being stuck, and wherein such FDA approved substances as laxatives, dilation chemicals, vinegar, or olive oil can be discharged, as in "a rescue exercise" feature to facilitate either disintegrating the food, or capsule component blockage, enlarge the aperture or existing gut diameter, or lubricate the gut to flush the total blockage substances of whatever nature, downstream. Included in this claim is the important capability of slow release of olive oil in the portion of the colon where most of the water has been extracted.

The passage of food products through the gut and their digestive process is a function of time, and one described method and process allows not only for a single snapshot sample testing, but a dynamic, time-dependent digestive process to be sampled, unobtrusively, and thereby analyzed, including the exposure of the same bait products from different pockets at delta time intervals apart, and controlled exposure times suitable to arrive at, for example, effective macro-level "reaction rate" or "rate-processing constants" for diagnostic, analysis, and modeling purposes. The significance of such capability could be manifested such that the "microbe-assisted, biochemical reaction rates of digestion" at a particular gut cross section "x" may be significant to healthy versus unhealthy conditions for diagnosis, as pertain to the conversion and absorption of nutrients, especially by compromised villi. Likewise, the rates of process creation of toxins are essential for determining causes of toxins associated with gluten sensitivities, Celiac or other diseases.

Capsule B can create and introduce time-dependent controlled processes and control variables to provide the feasibility for investigation of the time-dependent rates of process creation of toxins essential for determining causes of toxins associated with gluten sensitivities and Celiac. Thus, this Capsule B claimed capability also provides for and facilitates the feasibility of discovery of fundamental dynamic stages of protein transformation processes in the gut involving polypeptides, peptide bonds, ribosomes, tRNA, mRNA, at the molecular level, along with specific microbe strain roles, via in vitro investigation. Although for convenience, general reference herein has been made to microbes, microbiota, and bacteria strains associated with gut fluids, it also explicitly includes intraspecies, and however unlikely, other potential actors, such as, archaea, viruses, and retroviruses.

Capsule B may include a belt with pockets containing substances being delivered to the gut and also have a thin film covering, that when exposed to the gut environment, such as by opening a housing port, still maintains the contents inside the pocket sealed from the chyme and all gut content matter, in general.

The belt pocket film may be a specific design substance or material, that when attacked in some biochemical manner becomes dissolved, thereby exposing the contents of said belt pocket to the gut adjacent matter of whatever chemical or microbial content. The film of a specific indexed pocket may be of specific design substance to attract some specific strain or species of bacteria or other microbe as its specific preferred food, in contrast to the preferred foods of other strains or species of microbes. Whereas also, other adjacent pockets in the same belt may or may not contain the same exact substances, and the pocket covering films may be of other specific design substances to attract same or other microbes of a preferred food, and all pockets of which can be closed and preserved for in vitro sampling, testing and analysis.

A plurality of housing ports may be opened at the same time exposing said pocket film covers, wherein select indexed pockets may be exposed for different periods of time "t", or different gut positions "x" and upon individual commands each may be independently sealed and preserved for in vitro sampling, testing and analysis. One example for such a test being to determine the process by which autoimmune system toxins are produced, and to test an hypothesis that such toxins may be produced by cascaded events involving different species or strains of microbes processing different microbe byproducts, as an explanation for Celiac, gluten, or other protein, or other food product sensitivities.

Pocket covering film degradation may be sensed by various means, and said signals are monitored/stored/transmitted by telemetry for purposes of experiment decision making.

In addition to in vitro-analysis of in vivo-data and evidence, in vivo measurements are also simultaneously and continuously made within belt 3, recorded and transmitted to further correlate with said in vitro data analysis, as well as, correlate with extra body symptoms, observations and measurements, including, but not limited to, "stomach growling", bloating, acid reflux, diarrhea, dizziness, and dozens of other well documented symptoms associated with the complex food digestion and nutrient absorption processes.

The film on pocket(s) may be dissolved or ruptured by various means to expose cells-on-a-chip to gut fluids and microbes at some point of interest x, such as jejunum villi and micro-villi, to discover, identify, and locate sources, processes of creation, and chemical composition of toxins as may be first detected by cells-on-a-chip, and with further intimate chip contact actually identify and classify the toxin or its toxicity, and in the process, for example, discover the cause of such diseases as Celiac, or gluten, or other protein sensitivities of the autoimmune system. Said cells-on-the-chip may furthermore be the subject patient's own cells functioning as a sensor/transducer and the toxin substance and associated microbes captured/sampled.

Capsule B embodiments as a system constitutes a method and apparatus-based platform station from which a plurality of applications can be used to conduct a plethora of data gathering means, tests, analyses, diagnoses, and data reduction/interpretations to analyze the gastrointestinal tract processes and functions, and help diagnose its malfunctions.

The control of belt 3 position within Capsule B constitutes also a repositioning process capability that can be used for orienting the transmitting antenna for optimal extra body signal strength reception.

Various components may be made of FDA approved substances for use in biomedical applications, especially as manufactured by using 3-D or 4-D printing, and bio-nano-materials, and in addition, said construction materials may be made from regular food products normally consumed and digested by humans.

Measurements made within belt 3 pocket instruments may trigger alerts for decision making in general, or automated responses in an interactive manner.

Sensors in said belt pockets may be of a biosensor type, that incorporates biomaterials, microbes or hybrid sensors/transducers such as organs-on-a-chip.

Human safe substances deposited in belt 3 pockets and connected by one or more electrodes, including to the capsule exterior housing, create sufficient low-voltage potentials to constitute an in vivo battery of sufficient energy to power low-power requirement chips or other electronic/bio-electronic devices.

Instrumentation contained within belt 3 pockets may require sufficient low voltage and low energy levels to derive their power requirements from telemeter sources, or combined gut capsule and exterior body skin electrodes and applied potentials A new method of gut analysis, representation and modeling is created with embodiments of constructing numerical polynomial functions from a plurality of experimental data variables obtained from measurements of belt collected samples from Capsules A and B, as "Distribution Functions" of 1) gut length, 2) each other, 3) calculated variables, or 4)

other data sets. Likewise, said Distribution Functions can be created for a plurality of dependent variables as available from future data bases, such as, healthy or unhealthy, diseased, or other variables and correlated as a means of determining the sources of illnesses and diseases.

An in vivo tool may also provide for interactive biofeedback measurements of biochemical, bioelectric, muscular or other means, for example, autoimmune or brain responses to an in vivo perturbation of various means from within, or origin from, a belt pocket, and the immediate response is measured from another belt pocket.

Capsule B may be used as a research tool to explore, prove/disprove concepts and hypotheses pertaining to the digestion process, and create data that provides for detailed distribution functions that individually or in totality depict and characterize the digestion process for any specific food introduced at any point within the GI tract.

Capsule B as a research data mining tool, emulates the gut, and its contents characteristics in a sense, to capture more infinitesimal-like, large-volume data sets of various gut properties "as is" and "as perturbed", and some pockets within said belt system contain lab-in-a-chip based sensors for a multiplicity of variables and phenomena, and adjacent belt pockets contain huge data set storage provisions.

SUMMARY STATEMENT

It is noteworthy that these inventions herein described are intended in addition to analyzing the digestion process, to solve the causes of gut based and related diseases that have been identified and mystified researchers and medical practitioners around the world for over 2,000 years, and even research today is largely only involved with statistically researching and correlating the symptoms.

Recent estimates are that up to 70% of the U.S. population now has serious gut-based illnesses. Discomforts and life threatening diseases among so many people are troubling enough, and when coupled now with the dire burden of health care costs upon our economy, the importance of solving rather than treating these gut-based problems just in the United States alone, cannot in any way be overemphasized! These problems need to be solved here in the United States to reflect our national heritage of ingenuity and innovation, as well as, alleviate health budget problems, and so that as a generous and responsible nation, we can deliver these cures to the rest of the world. The invention herein disclosed reflects different and comprehensive methodology, with great results-oriented potential, to actually discover and solve the causes and provide cures for these problems. It is with this passion and purpose, this invention is submitted.

What is claimed is:

1. An interactive research device for at least one of perturbing, measuring and dispensing substances along an intestinal tract of a user, the device comprising:
   a capsule configured to be swallowed and passed through the intestinal tract, the capsule including:
      a housing defining an opening adapted to allow the substances to pass into and out of the housing,
      at least one sensor transducer,
      at least one belt disposed within the housing and defining a plurality of indentations, each of the indentations having a volume configured to perform at least one of collecting and dispensing the samples of matter, and at least one of a motor and an accuator disposed within the housing.

2. The device of claim 1, further comprising telemetry.

3. The device of claim 1, wherein the belt allows mass delivery, collection, and measurement of substances.

4. The device of claim 1, further comprising sensor, transducer and transmitter components.

5. The device of claim 1, wherein the indentations contain a sealed environment capable of storing solids, liquids and gases.

6. The device of claim 1, further comprising a time release mechanism.

7. The device of claim 1, wherein the indentations further comprise a protective film covering.

8. The device of claim 7, wherein the film dissolves when exposed to the intestinal tract environment.

9. The device of claim 7, wherein the film has an affinity or repulsion to substances.

10. The device of claim 3, wherein the delivery, collection and measurement of substances may be controlled independently.

11. The device of claim 7, wherein the film may be monitored.

12. The device of claim 7, wherein the film may be remotely controlled.

13. The device of claim 1, wherein the belt allows for repositioning of components.

14. The device of claim 3, wherein the sensor further comprises a triggering mechanism.

15. The device of claim 1, further comprising electrodes.

16. The device of claim 1, allowing feedback operations and control.

17. An interactive research method for perturbing and measuring responses along an intestinal tract of a user, the method comprising:
   providing a capsule configured to be swallowed and passed through the intestinal tract, the capsule including:
      a housing defining an opening adapted to allow samples of matter to pass into and out of the housing,
      at least one sensor transducer,
      a belt disposed within the housing and defining a plurality of indentations, each of the indentations having a volume configured to collect or dispense the samples of matter, and
      a motor or actuator disposed within the housing,
   inserting the capsule into the intestinal tract, and
   continuously monitoring and reacting to the responses.

18. The method of claim 17, further comprising active telemetry.

19. The method of claim 17, further comprising storing and processing the samples.

20. A research system comprising a capsule configured to be swallowed and passed through the intestinal tract, the capsule including:
   a housing defining an opening adapted to allow samples of matter to pass into and out of the housing,
   at least one sensor transducer,
   a belt disposed within the housing and defining a plurality of indentations, each of the indentations having a volume configured to collect or dispense the samples of matter, and an extra-body telemetry for processing data and generating a 3-dimensional image using the data.

* * * * *